United States Patent [19]

Ramachandran et al.

[11] Patent Number: 4,762,943

[45] Date of Patent: Aug. 9, 1988

[54] AROMATIZATION PROCESS

[75] Inventors: Venkataraman Ramachandran; John R. Maloney, both of Baton Rouge, La.

[73] Assignee: Ethyl Corporation, Richmond, Va.

[21] Appl. No.: 880,070

[22] Filed: Jun. 30, 1986

[51] Int. Cl.$^4$ .............................................. C07C 121/62
[52] U.S. Cl. ...................................... 558/423; 585/410
[58] Field of Search ................. 558/423; 585/410, 411

[56] References Cited

U.S. PATENT DOCUMENTS 3,184,498  5/1965  Bolhofer .............................. 558/423

OTHER PUBLICATIONS

Hoffman et al., *Tetrahedron Letters*, No. 17, pp. 1005–1008, (1964).
Reetz et al., *Liebigs Ann. Chem.*, (1978), pp. 1598–1606.
Mahuzier et al., *Bull. Soc. Chim. Fr.*, (1969), No. 2, pp. 687–690.

*Primary Examiner*—Anton H. Sutto
*Attorney, Agent, or Firm*—Patricia J. Hogan

[57] ABSTRACT

A dihydroaromatic compound is aromatized by intimately contacting it with a base selected from alkali metal, alkaline earth metal, and tetraalkylammonium hydroxides, alkoxides, carbonates, and bicarbonates in the presence of a hydrogen acceptor. In a preferred embodiment of the invention, the dihydroaromatic compound is a dihydronaphthalene bearing an electron-withdrawing substituent, e.g., a cyanodihydronaphthalene.

19 Claims, No Drawings

AROMATIZATION PROCESS

FIELD OF INVENTION

This invention relates to the aromatization of dihydroaromatic compounds.

Background

As disclosed in Morrison and Boyd, *Organic Chemistry*, Third Edition, Allyn and Bacon, Boston, pp. 974–976, and March, *Advanced Organic Chemistry*, Second Edition, McGraw-Hill, New York, pp. 1077–1078, it is known that hydroaromatic compounds can be aromatized in various ways. However, the known aromatization techniques are generally characterized by one or more disadvantages, such as high cost, the need for fairly severe conditions, the lack of sufficient ease in removing the aromatizing agent from the product, etc.

U.S. Pat. No. 4,590,010 (Ramachandran et al.) teaches that 6-alkoxy-1-cyano-3,4-dihydronaphthalenes can be aromatized by known techniques, such as by dehydrogenation in the presence of a palladium-on-carbon catalyst.

SUMMARY OF INVENTION

An object of this invention is to provide a novel aromatization process.

Another object is to provide such a process which utilizes an aromatizing agent that is economical, effective under mild conditions, and easily removed from the product.

These and other objects are attained by intimately mixing a dihydroaromatic compound with a base selected from alkali metal, alkaline earth metal, and tetraalkylammonium hydroxides, alkoxides, carbonates, and bicarbonates in the presence of a hydrogen acceptor so as to aromatize the hydroaromatic compound.

DETAILED DESCRIPTION

The compound that is aromatized in the practice of the present invention is a hydroaromatic compound, i.e., a compound which, as defined by Morrison and Boyd, contains the carbon skeleton of an aromatic system but too many hydrogen atoms for aromaticity, and more specifically a dihydroaromatic compound. Such compounds include compounds wherein the ring to be aromatized contains at least one double bond, e.g., dihydrobenzene, etc., but are generally compounds wherein the ring to be aromatized is fused to an aromatic ring, e.g., dihydroquinolines, dihydroisoquinolines, dihydroanthracenes, dihydrophenanthrenes, etc.

The hydroaromatic compounds that are most effectively aromatized in the practice of the invention are dihydroaromatic compounds, especially dihydronaphthalenes, and most especially such compounds bearing an electron-withdrawing substituent, such as $-N(CH_3)_3^+$, $-NO_2$, $-CN$, $-SO_3H$, $-COOH$, $-COOR$, $-CHO$, $-COR$, or X, wherein R is hydrocarbyl (e.g., an alkyl, cycloalkyl, aryl, alkaryl, or aralkyl group, generally such a group containing 1–10 carbons) and X is halo (i.e, chloro, bromo, fluoro, or iodo). Such compounds include, e.g., trimethylammoniumdihydronaphthalene hdrochlorides; nitro- and dinitrodihydronaphthalenes; cyanodihydronaphthalenes; dihydronaphthalenesulfonic acids; dihydronaphthoic acids; methyl, ethyl, propyl, butyl, pentyl, hexyl, phenyl, benzyl, and tolyl dihydronaphthoates; dihydronaphthaldehydes; methyl, ethyl, propyl, butyl, pentyl, hexyl, phenyl, benzyl, and tolyl naphthyl ketones; bromo-, chloro-, fluoro-, and iododihydronaphthalenes, etc., including such compounds which bear other substituents, such as additional electron-withdrawing groups or electron-donating groups, e.g., alkyl, alkoxy, amino, trifluoromethyl, The presence of at least one electron-withdrawing substituent on the ring appears to facilitate the reaction and is therefore desirable, but the particular nature of the substituent does not seem to be critical. There is also an apparent lack of criticality to the particular nature of any other substituents on the ring. However, it should be kept in mind that a reactive substituent can undergo reaction during the aromatization and that its presence can therefore influence the particular reaction conditions employed, as well as the product formed. For example, the presence of a substituent that is reactive with the base can make it necessary to use more base than would otherwise be employed, while the presence of a reducible substituent can obviate the need for using an additional hydrogen acceptor.

Since the objective of the invention is not to prepare any particular aromatic compound but to provide a more general, economically-attractive process for the aromatization of dihydroaromatic compounds, there are no generally-preferred starting materials in the usual sense. The preferred starting material in any instance will depend on the particular aromatic compound desired. However, as indicated above, there are factors that can make one percursor of a given aromatic compound preferable to another, e.g., cost, availability or the relative ease with which it can be prepared, the relative ease with which it can be aromatized, etc. Thus, e.g., considering the last of these factors, it is easier to aromatize a ring that is fused to an aromatic ring, and the presence of an electron-withdrawing substituent appears to facilitate aromatization.

Because of the utility of the products and the ease with which the precursors can be aromatized, a preferred embodiment of the invention is the aromatization of 3,4-dihydronaphthalenes having an electron-withdrawing substituent, especially a cyano group, in the 1-position. Exemplary of such dihydronaphthalenes are 1-cyano-3,4-dihydronaphthalene, 6-alkoxy-1-cyano-3,4-dihydronaphthalenes wherein the alkoxy group preferably contains 1–6 carbons, 6-alkyl-1-cyano-3,4-dihydronaphthalenes wherein the alkyl group preferably contains 1–6 carbons, the 5-bromo, 5-iodo, and 5-trifluoromethyl derivatives of the alkoxy and alkyl compounds, the corresponding compounds wherein the 1-substituent is one of the other electron-withdrawing substituents mentioned above, etc. The cyano compounds, especially those bearing a methoxy or other alkoxy substituent in the 5-position, are of particular interest because of their utility in a modification of the process of Ramachandran et al., the teachings of which are incorporated herein by reference.

The base employed as an aromatizing agent may be alkali metal, alkaline earth metal, or tetraalkylammonium hydroxide, alkoxide, carbonate, or bicarbonate. When the cation is a metal atom, it may be lithium, sodium, potassium, rubidium, cesium, calcium, strontium, or barium. When it is a tetraalkylammonium group, it may be any such group in which the alkyl groups are the same or different, straight-chain or branched, and contain about 1–20 carbons, usually about 1-12 carbons, such as tetramethyl, tetraethyl, tetrapropyl, tetrabutyl, tetrapentyl, tetrahexyl, tetraheptyl, methyltributyl, methyltrioctyl, methyltrialkyl($C_8$–$C_{10}$), butyltripropyl, heptyltriethyl, octyltriethyl, dodecyltrimethyl, dodecyltriethyl, tetradecyltrimethyl, and hexadecyltrimethylammonium groups, etc. Any alkoxide of such cations may be used, but those containing 1-4 carbons, e.g., methoxides, ethoxides, isopropoxides, and t-butoxides, are apt to be preferred over higher alkoxides because of availability. Also, as already indicated, the base may be a carbonate or bicarbonate. The hydroxides, however, are preferred, and the most preferred bases are the alkali metal hydroxides, especially sodium or potassium hydroxide.

The base may be employed in any form that permits its intimate admixture with the dihydroaromatic compound, either a powder or an aqueous solution being apt to be preferred. The amount of base required varies with various factors, such as the presence or absence of reactive substituents on the ring of the dihydroaromatic compound, the intimacy of admixture obtainable under the reaction conditions, etc. However, even though smaller amounts are frequently operable, the amount of base used is generally at least about 0.05 mol, most commonly at least about 0.1 mol, per mol of hydroaromatic compound. There is no maximum to the amount that may be used.

As mentioned above, the hydrogen acceptor may be the dihydroaromatic compound itself when that compound contains at least one reducible group. However, the acceptor is more commonly a separate compound, generally a nitro compound, and preferably a nitroarene capable of serving as a solvent. Exemplary of utilizable hydrogen acceptors are nitroalkenes, such as nitroethane, 1-nitrohexane, 3-nitro-2,2-dimethylbutane, 2-nitro-2-methylpentane, etc., and nitroarenes, such as nitrobenzene, 2-, 3-, and 4-nitrotoluenes, 2- and 4-nitroethylbenzenes, 2-nitro-1,3,5-trimethylbenzene, nitronaphthalenes, etc., with nitrobenzene being especially preferred. The amount of hydrogen acceptor employed should be at least an equivalent amount and can be much higher, since there is no maximum to the amount that may be used.

In order to facilitate the intimate admixture of the reactants, it is preferable to conduct the aromatization in the presence of a solvent. When a solvent is employed, it may be any normally liquid organic material capable of solvating the dihydroaromatic compound, but it is preferably a compound capable of serving both as a solvent and as a hydrogen acceptor. It is most preferably a nitroarene solvent such as those mentioned above, especially nitrobenzene.

Especially when the base is incorporated as an aqueous solution into a solution of the dihydroaromatic compound, it is apt to be desirable or even necessary to conduct the aromatization in the presence of a phase transfer agent. The phase transfer agent, when employed, may be any such agent capable of solubilizing the cation of the base in the solvent employed for the dihydroaromatic compound. However, it is usually a crown ether such as 12-crown-4, 15-crown-5, 18-crown-6, etc.; an alcohol such as methanol, ethanol, etc.; a polyalkylene glycol such as PEG 600, etc.; an alkylammonium or alkylphosphonium salt, etc. The phase transfer agents most commonly used are the alkylammonium and alkylphosphonium salts, especially the bromides or other halides, such as tetramethyl, tetraethyl, tetrapropyl, tetrabutyl, tetrapentyl, tetrahexyl, tetraheptyl, methyltributyl, methyltrioctyl, methyltrialkyl($C_8$–$C_{10}$), butyltripropyl, heptyltriethyl, octyltriethyl, dodecyltrimethyl, dodecyltriethyl, tetradecyltrimethyl, and hexadecyltrimethylammonium bromides, chlorides, iodides, and fluorides; trimethyl, triethyl, methyldiisopropyl, and ethyldiisopropylammonium hydrogen halides; the corresponding alkylphosphonium halides, etc. The preferred phase transfer agents are tetraalkylammonium halides wherein the alkyl groups contain 1-20, most commonly 1-12, carbons. Particularly preferred is tetrabutylammonium bromide. When employed, the phase transfer agent is usually used in a concentration of about 0.001-10 mol precent, based on the amount of hydroaromatic compound.

In conducting the aromatization, a pure or crude dihydroaromatic compound is intimately contacted with the base, hydrogen acceptor, and any additional ingredients and maintained in intimate contact by stirring the reaction mixture. It may be necessary to heat the mixture initially to start the reaction when the ingredients have been contacted at a temperature below 15° C. but, once started, the reaction is exothermic and normally does not require additional external heating. However, when the reaction appears sluggish, additional heat can be applied to provide reaction temperatures up to about 100° C.

After completion of the reaction, the aromatic product may be recovered by conventional means and/or converted to a desired derivative, such as the pharmaceutical materials of U.S. Pat. No. 4,439,617 (Sestanj et al.).

The invention is advantageous as a commercially-attractive process for aromatizing dihydroaromatic compounds and is especially advantageous as a means of aromatizing 3,4-dihydronaphthalenes which are useful as precursors of the pharmaceuticals taught by Sestanj et al.

The following examples are given to illustrate the invention and are not intended as a limitation thereof.

EXAMPLE I

A 50-mL sample of a 14% solution of crude 6-methoxy-1-cyano-3,4-dihydronaphthalene (6-MCDN) in nitrobenzene (0.04 mol of 6-MCDN) was cooled to 4° C. in an ice bath, 0.004 mol of powdered KOH was added with rapid stirring, and the mixture was warmed to 15° C. After one hour, GC analysis showed that all of the 6-MCDN had been converted to 6-methoxy-1-cyanonaphthalene (6-MCN) and part of the nitrobenzene had been converted to azoxybenzene.

EXAMPLE II

Another 50-mL sample of the crude 6-MCDN solution of Example I was stirred rapidly for 30 minutes with 50 mL of 10% aqueous KOH. GC analysis showed that the reaction mixture contained 6-MCN and 6-MCDN in a ratio of 70:30. After an additional 30 minutes of stirring at room temperature, no 6-MCDN remained. Analysis also showed that part of the nitrobenzene had been converted to azoxybenzene.

EXAMPLE III

A crude 6-MCDN was prepared by reacting 6-methoxytetralone (6-MT) with NaCN in the presence of aluminum chloride, tetrabutylammonium bromide, a small amount of concentrated HCl, and nitrobenzene at 90°–95° C. for six hours. After the reaction had been determined to be 90% complete, the reaction mixture was cooled to room temperature and mixed with an equal volume of 20% NaOH. The temperature rose to 45°–50° C., and the reaction mixture was maintained at that temperature for one hour. VPC analysis showed that substantially all of the 6-MCDN had been aromatized and that the reaction mixture contained 2.7 area % of 6-MT, 67 area % of 6-MCN, 22.8 area % of azoxybenzene, and 7.4 area % of unknowns.

It is obvious that many variations may be made in the products and processes set forth above without departing from the spirit and scope of this invention.

We claim:

1. A process which comprises intimately mixing a 6-alkoxy-1-cyano-3,4-dihydronaphthalene with a base selected from alkali metal and tetraalkylammonium hydroxides and alkoxides in the presence of a hydrogen acceptor so as to aromatize the dihydronaphthalene.

2. The process of claim 1 wherein the base is a hydroxide.

3. The process of claim 2 wherein the base is an alkali metal hydroxide.

4. The process of claim 3 wherein the base is sodium hydroxide.

5. The process of claim 3 wherein the base is potassium hydroxide.

6. The process of claim 1 wherein the base is employed as an aqueous solution.

7. The process of claim 1 wherein the hydrogen acceptor is a nitroarene solvent.

8. The process of claim 7 wherein the hydrogen acceptor is nitrobenzene.

9. The process of claim 1 wherein the aromatization is conducted in the presence of a phase transfer agent.

10. The process of claim 9 wherein the phase transfer agent is an alkylammonium salt.

11. The process of claim 10 wherein the phase transfer agent is a tetraalkylammonium halide in which the alkyl groups contain 1–20 carbons.

12. The process of claim 11 wherein the phase transfer agent is tetrabutylammonium bromide.

13. A process which comprises intimately mixing a 6-alkoxy-1-cyano-3,4-dihydronaphthalene with an alkali metal hydroxide in the presence of a nitroarene solvent so as to aromatize the dihydronaphthalene.

14. The process of claim 13 wherein the hydroxide is sodium or potassium hydroxide and the nitroarene is nitrobenzene.

15. The process of claim 14 wherein the hydroxide is potassium hydroxide.

16. A process which comprises intimately mixing a 6-alkoxy-1-cyano-3,4-dihydronaphthalene with an aqueous alkali metal hydroxide in the presence of a nitroarene solvent and a phase transfer agent so as to aromatize the dihydronaphthalene.

17. The process of claim 16 wherein the hydroxide is sodium or potassium hydroxide, the nitroarene is nitrobenzene, and the phase transfer agent is an alkylammonium salt.

18. The process of claim 17 wherein the hydroxide is sodium hydroxide and the phase transfer agent is a tetraalkylammonium halide in which the alkyl groups contain 1–20 carbons.

19. The process of claim 18 wherein the phase transfer agent is tetrabutylammonium bromide.

* * * * *